(12) United States Patent
Horesh

(10) Patent No.: US 10,802,182 B2
(45) Date of Patent: Oct. 13, 2020

(54) TECHNOLOGIES FOR ENHANCING CONTRAST OF AN ILLUMINATION MARKER

(71) Applicant: Intel Corporation, Santa Clara, CA (US)

(72) Inventor: Nizan Horesh, Caesarea (IL)

(73) Assignee: Intel Corporation, Santa Clara, CA (US)

( * ) Notice: Subject to any disclaimer, the term of this patent is extended or adjusted under 35 U.S.C. 154(b) by 122 days.

(21) Appl. No.: 15/787,695

(22) Filed: Oct. 18, 2017

(65) Prior Publication Data

US 2019/0113662 A1     Apr. 18, 2019

Related U.S. Application Data

(60) Provisional application No. 62/573,679, filed on Oct. 17, 2017.

(51) Int. Cl.
| | | |
|---|---|---|
| *G02B 5/12* | (2006.01) | |
| *G02B 5/126* | (2006.01) | |
| *F21V 3/02* | (2006.01) | |
| *F21K 9/64* | (2016.01) | |
| *G02B 5/02* | (2006.01) | |
| *F21V 19/00* | (2006.01) | |
| *A61B 5/11* | (2006.01) | |
| *G06F 3/03* | (2006.01) | |
| *G02B 5/22* | (2006.01) | |
| *G02B 5/00* | (2006.01) | |
| *G06K 9/20* | (2006.01) | |
| *G02B 1/04* | (2006.01) | |

(52) U.S. Cl.
CPC ............ *G02B 5/126* (2013.01); *A61B 5/1127* (2013.01); *F21K 9/64* (2016.08); *F21V 3/02* (2013.01); *F21V 19/006* (2013.01); *G02B 5/003* (2013.01); *G02B 5/0236* (2013.01); *G02B 5/12* (2013.01); *G02B 5/22* (2013.01); *G06F 3/0304* (2013.01); *G02B 1/04* (2013.01); *G02B 2207/123* (2013.01); *G06K 9/2054* (2013.01)

(58) Field of Classification Search
CPC ........ G02B 5/126; G02B 5/0236; G02B 1/04; F21V 19/006; F21V 3/02; F21K 9/64; G06K 9/2054; C08L 69/00
USPC ......................................... 359/515
See application file for complete search history.

(56) References Cited

U.S. PATENT DOCUMENTS

2012/0199929 A1*  8/2012  Kamijyo ................ G02B 5/208
                                                                257/432
2017/0134660 A1*  5/2017  Truong .............. H04N 5/23293

* cited by examiner

*Primary Examiner* — Euncha P Cherry
(74) *Attorney, Agent, or Firm* — Barnes & Thornburg LLP

(57) ABSTRACT

An illumination marker includes a light source and an optical attenuation cover coupled to the light source. The optical attenuation cover is configured to attenuate an intensity of light that passes through the optical attenuation cover based on a length of an optical path of the light through the optical attenuation cover. In some embodiments, the optical attenuation cover may be embodied as a physical barrier cover and include light-blocking structures. Additionally, in some embodiments, the illumination maker may include a diffusive or retro-reflective core rather than the light source.

23 Claims, 8 Drawing Sheets

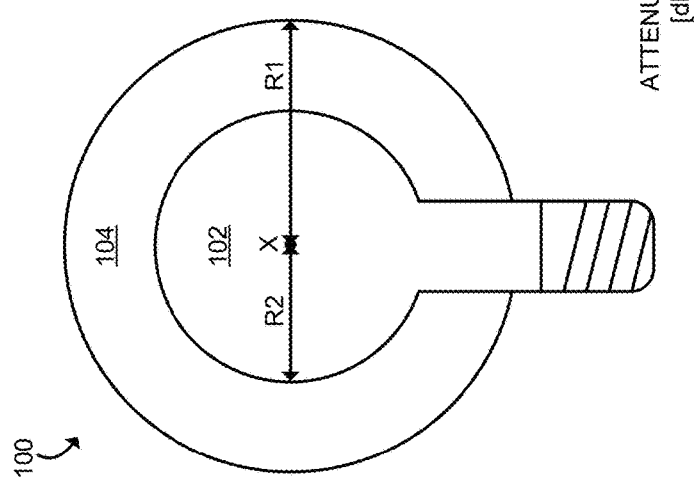
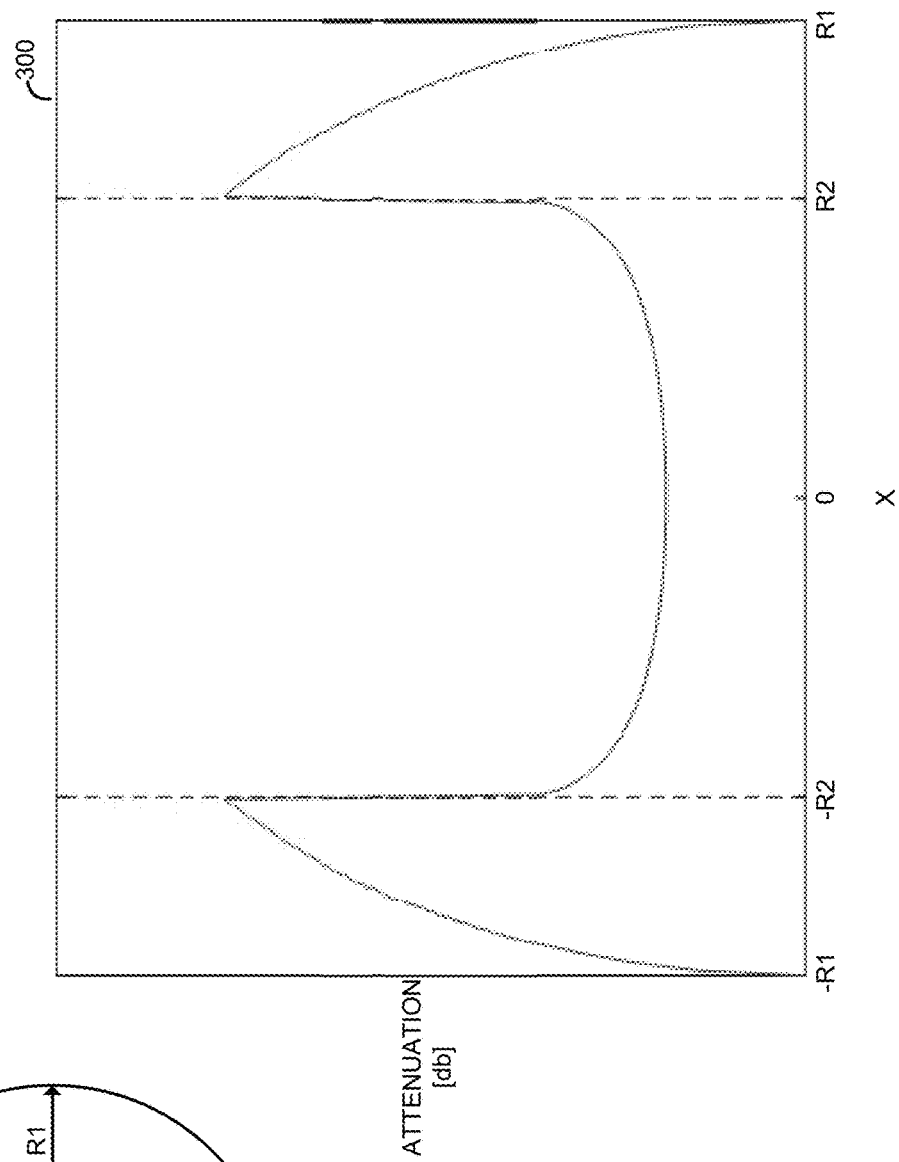
FIG. 3

TECHNOLOGIES FOR ENHANCING CONTRAST OF AN ILLUMINATION MARKER

CROSS-REFERENCE TO RELATED APPLICATIONS

The present application claims the benefit of U.S. Provisional Patent Application No. 62/573,670, entitled "TECHNOLOGIES FOR ENHANCING CONTRAST OF AN ILLUMINATION MARKER," which was filed on Oct. 17, 2017.

BACKGROUND

Illumination markers are used in various tracking technologies to track associated objects in three-dimensional space. Typical illumination markers produce an amount of light, which is tracked using an image-producing device such as a camera. For example, in some gaming systems, illumination markers are used to track the position of a game controller in three-dimensional space. To properly track the illumination marker, the marker must be discernable from any surrounding background light, regardless of the point-of-view of the illumination marker relative to the camera. However, if the background light is of a sufficient intensity, the illumination marker may be indistinguishable from the background light, which may cause difficulties in tracking the illumination marker.

Traditional tracking systems may use selective colored lights or infra-red light markers to combat the possibility of the background light washing out the illumination marker. Alternatively, some tracking systems may use a complicated pattern of lights as an illumination marker or use active objects (e.g., "smart" controllers) as the tracked device.

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

FIG. 3 is an illustrative graph showing an example of optical attenuation of the optical attenuation cover of FIGS. 1 and 2;

DETAILED DESCRIPTION OF THE DRAWINGS

Figure 1:
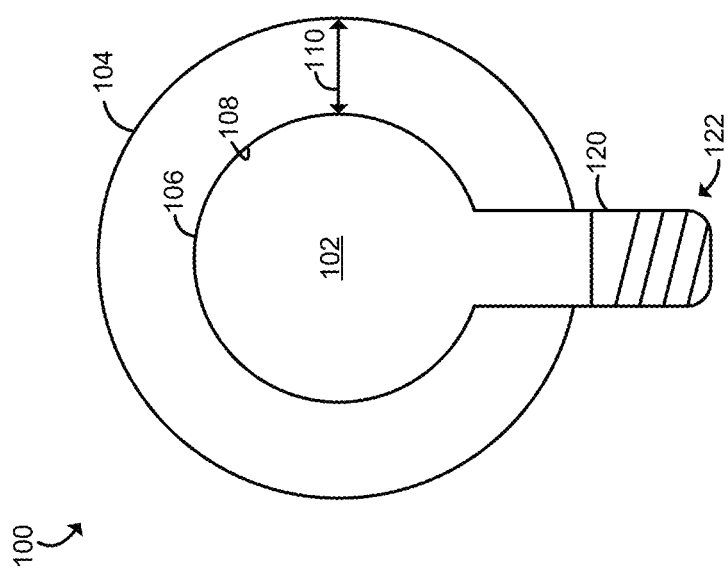
FIG. 1 is a cross-sectional, elevational view of at least one embodiment of an illumination marker including an optical attenuation cover.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, an illumination marker 100 includes a light source 102 and an optical attenuation cover 104, which covers the light source 102. The light source 102 may be embodied as any type of illumination device or source including, but not limited to, an incandescent light, a light emitting diode, or other light-producing device. In some embodiments, the light source 102 may be configured to generate light of a wide spectrum in an omni-directional manner; however, in other embodiments, the light source 102 may be configured to generate light of a narrow spectrum (e.g., of a specific wavelength band) and/or in a uni-directional manner as discussed below. In some embodiments, the light source 102 may include a shell 106, such as a glass shell, that houses an internal light generating device (e.g., an electric filament). However, in other embodiments, an inner wall 108 of the optical attenuation cover 104 may form the shell of the light source 102.

As shown in FIG. 1, the optical attenuation cover 104 covers or surrounds the light source 102. For example, in some embodiments, the optical attenuation cover 104 may be directly attached to the light source 102 (e.g., to a shell 106 of the light source 102). Alternatively, in other embodiments, the optical attenuation cover 104 may be formed to cover the light source 102 but be spaced away from the shell 106 of the light source 102 such that be spaced apart from the light source 102, while still covering the light source 102.

As discussed in more detail below, the optical attenuation cover 104 is configured to attenuate or reduce the intensity of light that passes through the cover 104. As such, the optical attenuation cover 104 may have a thickness 110 based on the amount of desired attenuation. In the illustrative embodiment, the thickness 110 is large relative to the radius of the light source 102. For example, the thickness 110 may be substantially equal to the radius of the light source 102 in some embodiments).

The illustrative illumination marker 100 also includes a base 120, which includes a number of threads 122. The base 120 and threads 122 facilitate the coupling of the illumination marker 100 to a corresponding socket. Of course, the shape and size of the base 120 and/or threads 122 may differ based on the type of socket and/or use of the illumination marker 100. Additionally, although the illumination marker 100 is embodied as a spherical marker in the illustrative embodiment of FIG. 1 (i.e., the light source 102 and the optical attenuation cover 104 are spherical in shape), it should be appreciated that the illumination marker 100 may have other geometrical shapes in other embodiments depending on the intended use of the illumination marker 100. For example, the light source 102 and/or the optical attenuation cover 104 may have a cylindrical, rectangular, or other geometrical shape.

Figure 2:
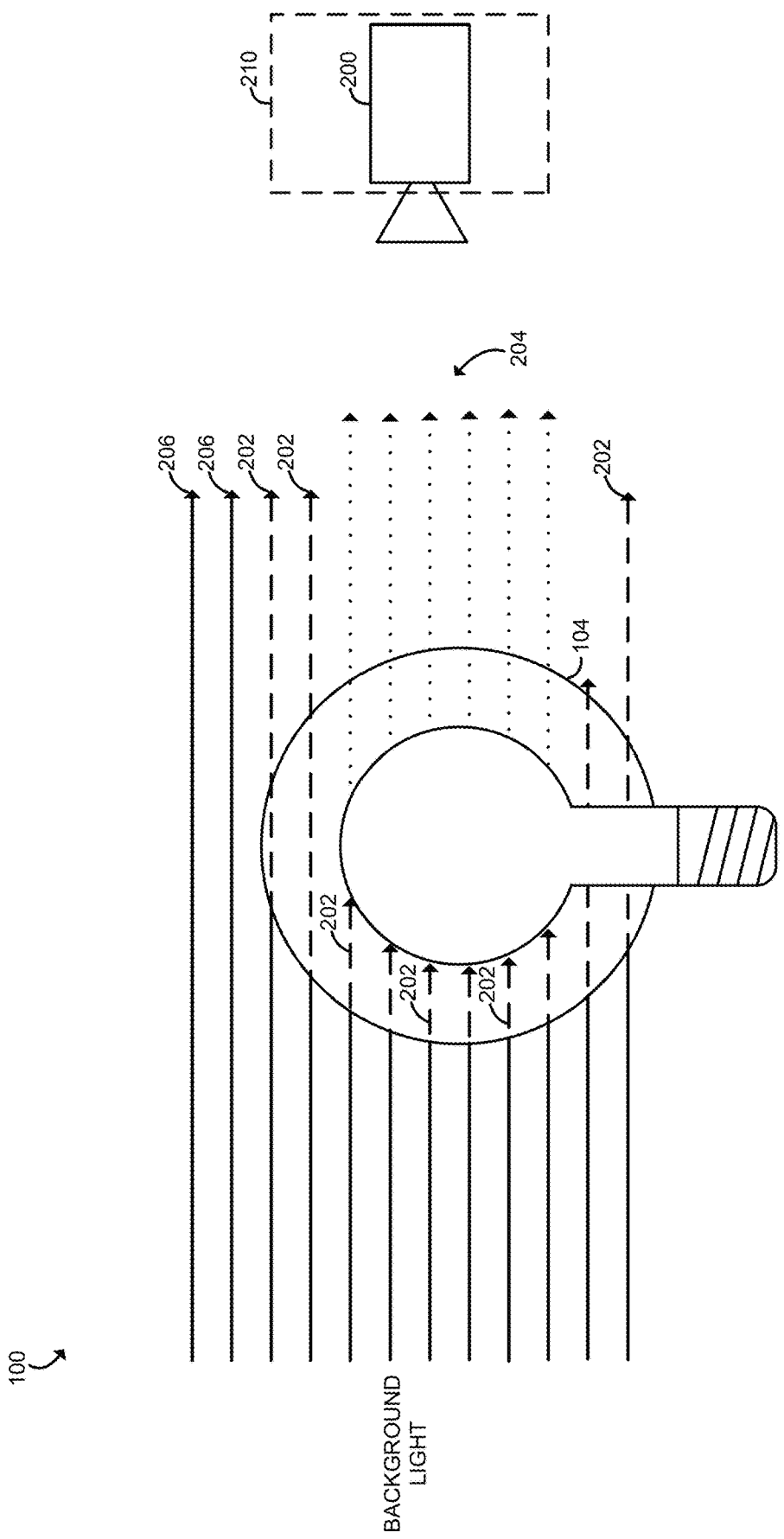
FIG. 2 is a cross-sectional, elevational view of the illumination marker of FIG. 1 illustrating the attenuation of background light passed through the optical attenuation cover.

Referring now to FIG. 2, the optical attenuation cover 104 is configured to attenuate light passing through the cover 104. As such, the optical attenuation cover 104 may be formed from any type and shape of material capable of attenuating the intensity of light as the light travels through the optical attenuation cover 104. For example, in the illustrative embodiment, the optical attenuation cover 104 is formed from a polycarbonate material configured to absorb an amount of light that travels through the cover 104. Such polycarbonate material may be further colored or otherwise translucent in some embodiments.

It should be appreciated that, because the background light travels a further distance through the optical attenuation cover 104 than light generated by the light source 102, the attenuation of the background light is greater than any attenuation of the light source 102. As such, the background light traversing through the optical attenuation cover 104 (illustrated in FIG. 2 as dashed light rays 202) will have a significantly lower intensity than the light generated by the light source 102 (illustrated in FIG. 2 as dotted light rays 204), as well as the background light that has not traversed through the optical attenuation cover 104 (illustrated in FIG. 2 as solid light rays 206). That is, the intensity of the background light rays 202 traversing through the optical attenuation cover 104 is attenuated by a greater amount than the light rays 204 generated by the light source 102 because the light rays 202 travel a greater distance through the optical attenuation cover 104 than the light rays 204. As discussed in more detail below, the attenuation of the optical attenuation cover 104 may be logarithmic based on the distance traveled. As such, the effective attenuation may be significantly different for different distances traveled through the optical attenuation cover 104.

Due to the differences in light intensity between the background light (light rays 202) and the light generated by the light source 102 (light rays 204), a camera 200 or other image-producing device generates images having a higher contrast between the light source 102 and the background light. That is, the reduction of the intensity of the background light that has traversed through the optical attenuation cover 104 (i.e., light rays 202) facilitates the discernibility of the outline of the optical attenuation cover 104 in images generated by the camera 200. In such images, as shown and discussed in regard to FIG. 5 below, the optical attenuation cover 104 may appear as a two-dimensional cover around the light source 102, which separates the light source 102 from any background light allowing the light source 102 to be more easily discerned from the background light and tracked accordingly.

The camera 200 may be embodied as any type of image-producing device such as a still image camera, video camera, or the like. In the illustrative embodiment, the camera 200 forms a portion of a tracking system 210 to track the location of the illumination marker 100 (or an objected to which the illumination marker 100 is coupled or otherwise associated with). For example, the camera 200 may form a portion of a tracking system 210 of a game console, and the illumination marker 100 may be attached to, or otherwise form a portion of, a game controller that is tracked by the tracking system 210 of the game console. Of course, the illumination marker 100 may be used to track other devices or objects in other embodiments.

Referring now to FIG. 3, in the illustrative embodiment, the optical attenuation of the optical attenuation cover 104 is logarithmic relative to the path length of light traversing therethrough. For example, for an illustrative illumination marker 100 including a spherical light source 102 having a radius $R_2$ and an optical attenuation cover 104 having a radius $R_1$, the optical pathway L can be defined as:

$$L(r) = \begin{cases} 2R_1\sqrt{1-\left(\frac{r}{R_1}\right)^2} & r > R_2 \\ R_1\sqrt{1-\left(\frac{r}{R_1}\right)^2} - R_2\sqrt{1-\left(\frac{r}{R_2}\right)^2} & r < R_2 \end{cases}$$

wherein r is the distance from the center X of the spherical light source 102, along a plane defined by the camera 200 (assuming, for simplicity and clarity, there is no refraction of light). The graph 300 illustrates the light attenuation of light traversing through the illustrative illumination marker 100 along a central cross-section. As shown in FIG. 3, the attenuation between R2 and R1 (i.e., the attention of the optical attenuation cover 104) is logarithmic. As such, a difference in optical path length results in a significant difference in attenuation. Accordingly, because the background light travels a greater distance through the optical attenuation cover 104 (i.e., has a greater optical path length) than the light generated by the light source 102, the background light is attenuated a greater amount than the light generated by the light source 102. The greater attenuation of the background light traversing the optical attenuation cover 104 increases the contrast between the optical attenuation cover 104, the light source 102, and other background light that has not traversed the optical attenuation cover 104 in a images generated by the camera 200 or other image-producing device. As discussed in more detail below in regard to FIG. 5, the optical attenuation cover 104 may appear as an outline of the light source 102, which increases the contrast between the light source 102 and the background light.

Although the illustrative optical attenuation cover 104 has been described above as attenuating light across a wide spectrum, the optical attenuation cover 104 may be configured to selectively attenuate light in some embodiments. For example, the optical attenuation cover 104 may be formed from a material capable of attenuating all light except for a particular wavelength or small band of wavelengths. In such embodiments, the light source 102 may be configured to generate light at the particular wavelength (e.g., a wavelength within the defined pass-band of wavelengths) such that the light generated by the light source 102 is attenuated by the optical attenuation cover 104 only by a small amount relative to the attenuation of the background light, which is generally wide-band. For example, the light source 102 may be configured to generate light having a wavelength of 850 nanometers (nm), while the optical attenuation cover 104 is configured to attenuate light of wavelengths other than 850 nm (or a defined band of wavelengths around 850 nm).

Figure 4:
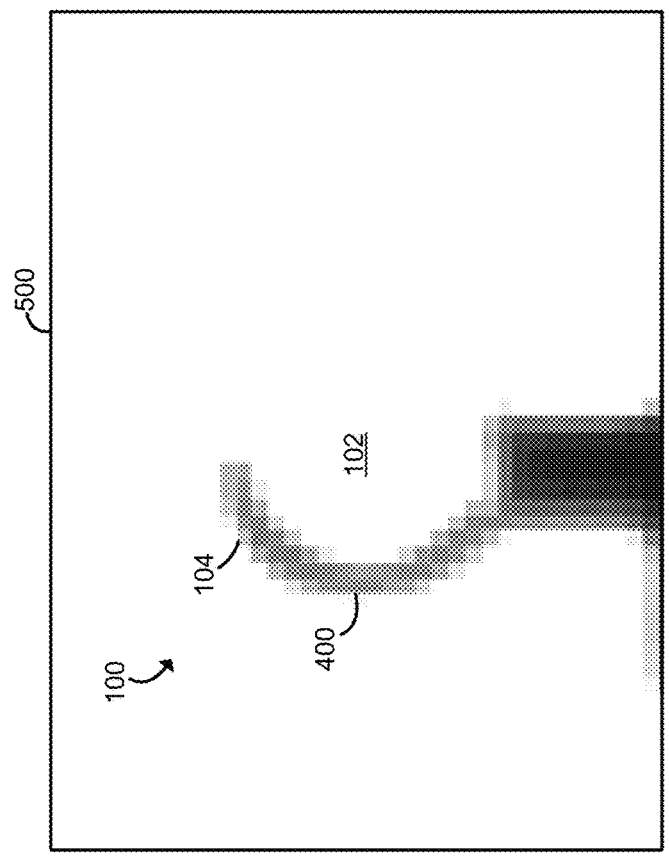
FIG. 4 is a simplified illustration of one embodiment of the illumination marker of FIGS. 1 and 2 with an optical attenuation half-cover attached to the light source.
Figure 5:
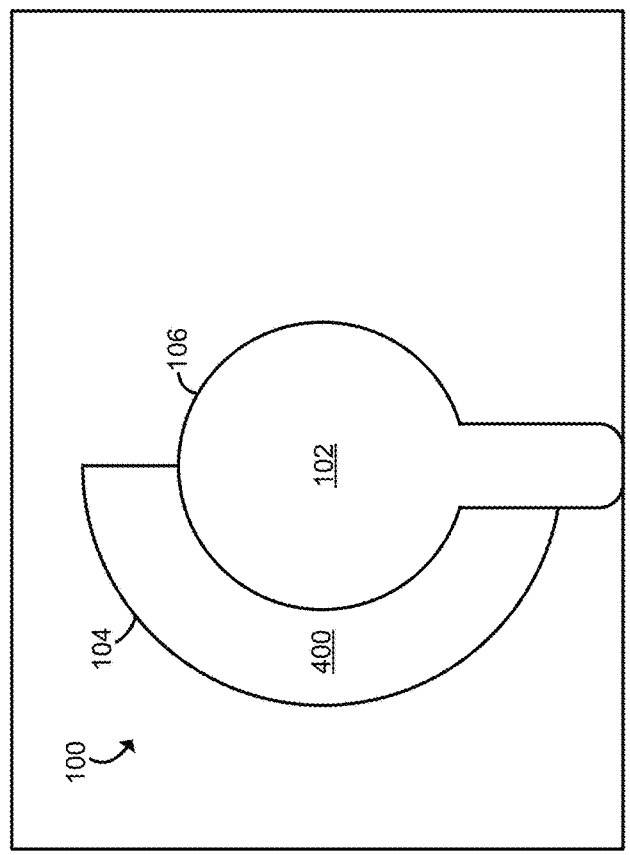
FIG. 5 is an image of the illumination marker of FIG. 4 illustrating the contrast differences between the portion of the illumination marker covered by the optical attenuation half-cover relative to the uncovered portion of the illumination marker.

Referring now to FIG. 4, an illustrative illumination marker 100 is shown with the optical attenuation cover 104 embodied as an optical attenuation half-cover 400. That is, the optical attenuation half-cover 400 covers only half of the light source 102. In the illustrative embodiment, the light source 102 includes the shell 106, and the optical attenuation half-cover 400 may be attached to a half-portion of the shell 106. An image 500 of the illumination marker 100 of FIG. 4 generated by the camera 200 or other imaging device is shown in FIG. 5. In the image 500, the optical attenuation half-cover 400 is discernable from the background light and the light source 102. As such, the optical attenuation half-cover 400 creates a contrast between the background light and the light generated by the light source 102 by creating an "outline" of the light source 102. Conversely, the half-portion of the light source 102 not covered by the optical attenuation half-cover 400 has a relatively low contrast relative to the background light and, as such, is indiscernible from the background light. Accordingly, it should be appreciated that, because the optical attenuation cover 104 increases the contrast between the light source 102 and background light, an illumination marker including the optical attenuation cover 104 may be more easily discernable against background light and, as such, easier to track by a corresponding tracking system.

Figure 6:
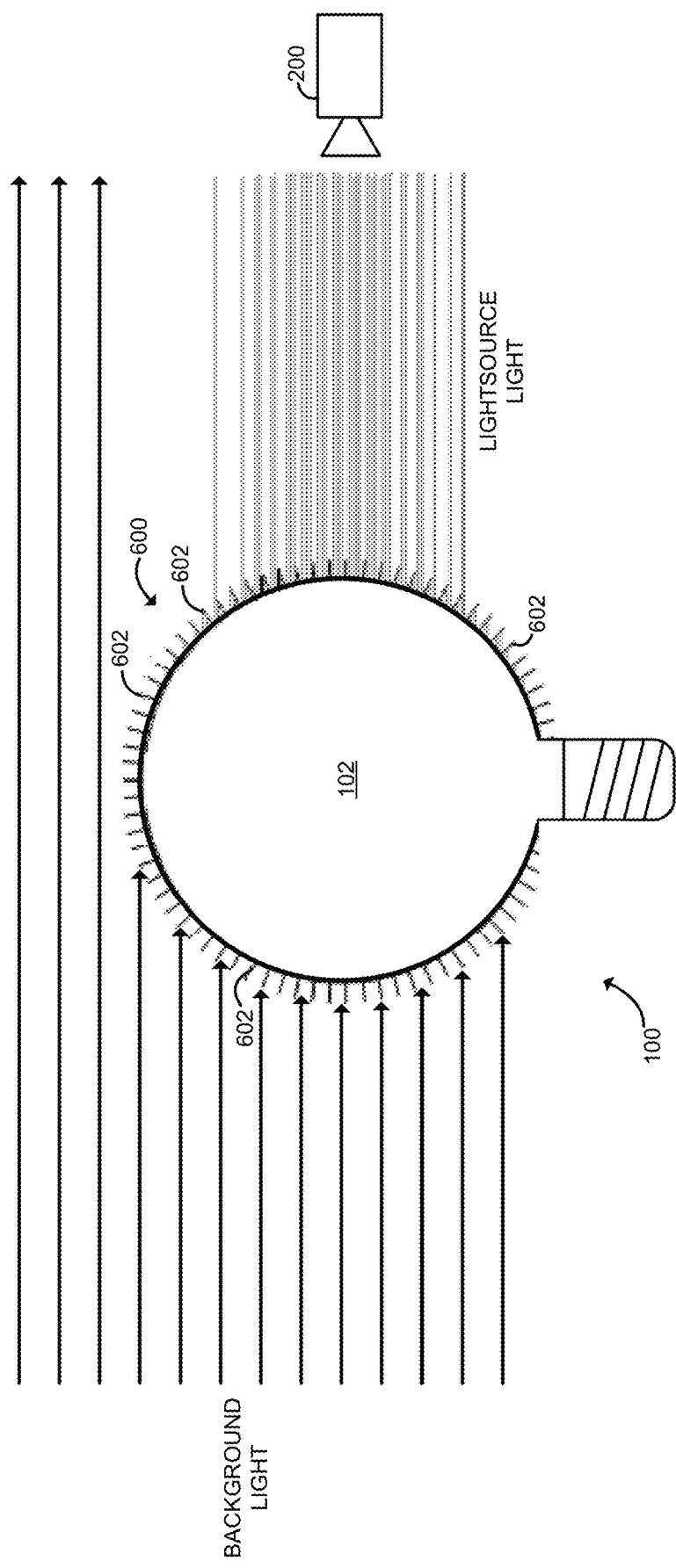
FIG. 6 is a cross-sectional, elevational view of at least one additional embodiment of an illumination marker including a physical barrier cover.

Referring now to FIG. 6, in some embodiments, the optical attenuation cover 104 may be embodied as a physical barrier cover 600. The physical barrier cover 600 includes multiple light-blocking structures or vanes 602 configured to block or obstruct background light, while allowing some amount of light generated by the light source 102 to escape through the structures or vanes 602 relatively unobstructed. It should be appreciated that while some of the light generated by the light source 102 is blocked or otherwise obstructed by the light-blocking structures or vanes 602, a portion of the light generated by the light source 102 is unobstructed or significantly unobstructed by the physical barrier cover 600. The physical barrier cover 600 may form the shell of the light source 102, as shown in FIG. 6, or may be attached to or otherwise cover a shell of the light source 102. Additionally, it should be appreciated that only light in the x-axis is shown in FIG. 6 for clarity of the drawing. However, in use, the physical barrier cover 600 allows light from the light source 102 to pass unobstructed in other directions toward the location of the camera 200 (e.g., should the camera 200 be moved relative to the illumination marker 100.) That is, in the illustrative embodiment, the light-blocking structures or vanes 602 allow that portion of the light generated by the light source that is axial with the camera 200, while blocking or obstructing light that is non-axial with the camera 200.

Figure 7:
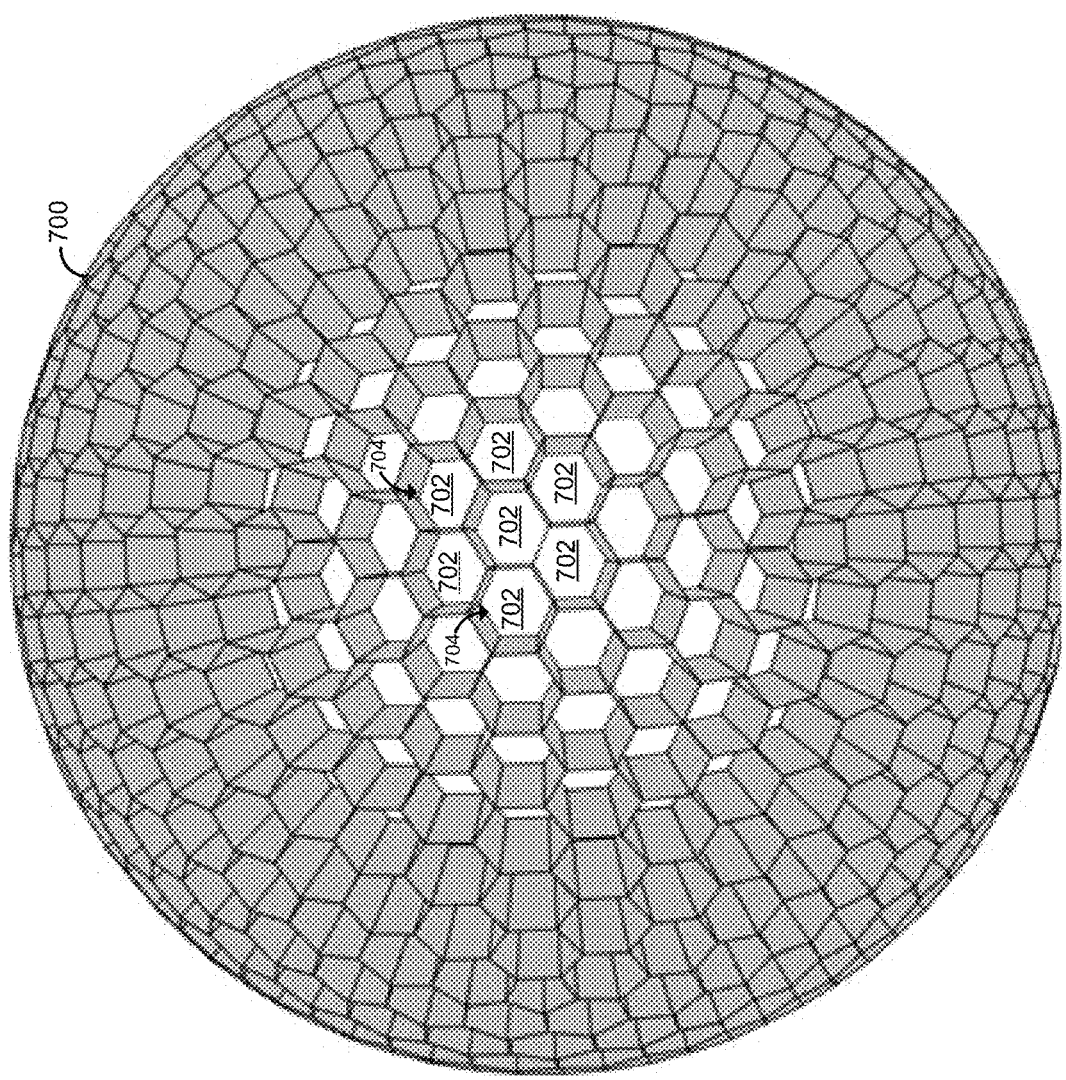
FIG. 7 is an elevational view of at least one embodiment of the physical barrier cover of the illumination marker of FIG. 6.

The physical barrier cover 600 may be embodied as any type cover capable of being positioned on or over the light source 102 and obstructing background light. In the illustrative embodiment of FIG. 7, for example, the physical barrier cover 600 is embodied as a honeycomb-shaped physical barrier cover 700 and includes a large number of polygonal structures 702 (illustratively hexagons and pentagons) that are configured to obstruct or block background light while allowing some light generated by the light source 102 to pass (e.g., depending on the relative location of the camera 200). For example, each of the polygonal structures 702 include a corresponding aperture 704 through which the light generated by the light source 102 can pass. Of course, the physical barrier cover 700 may include barrier structures of other geometric shapes (e.g., triangular shape) in other embodiments.

Figure 8:
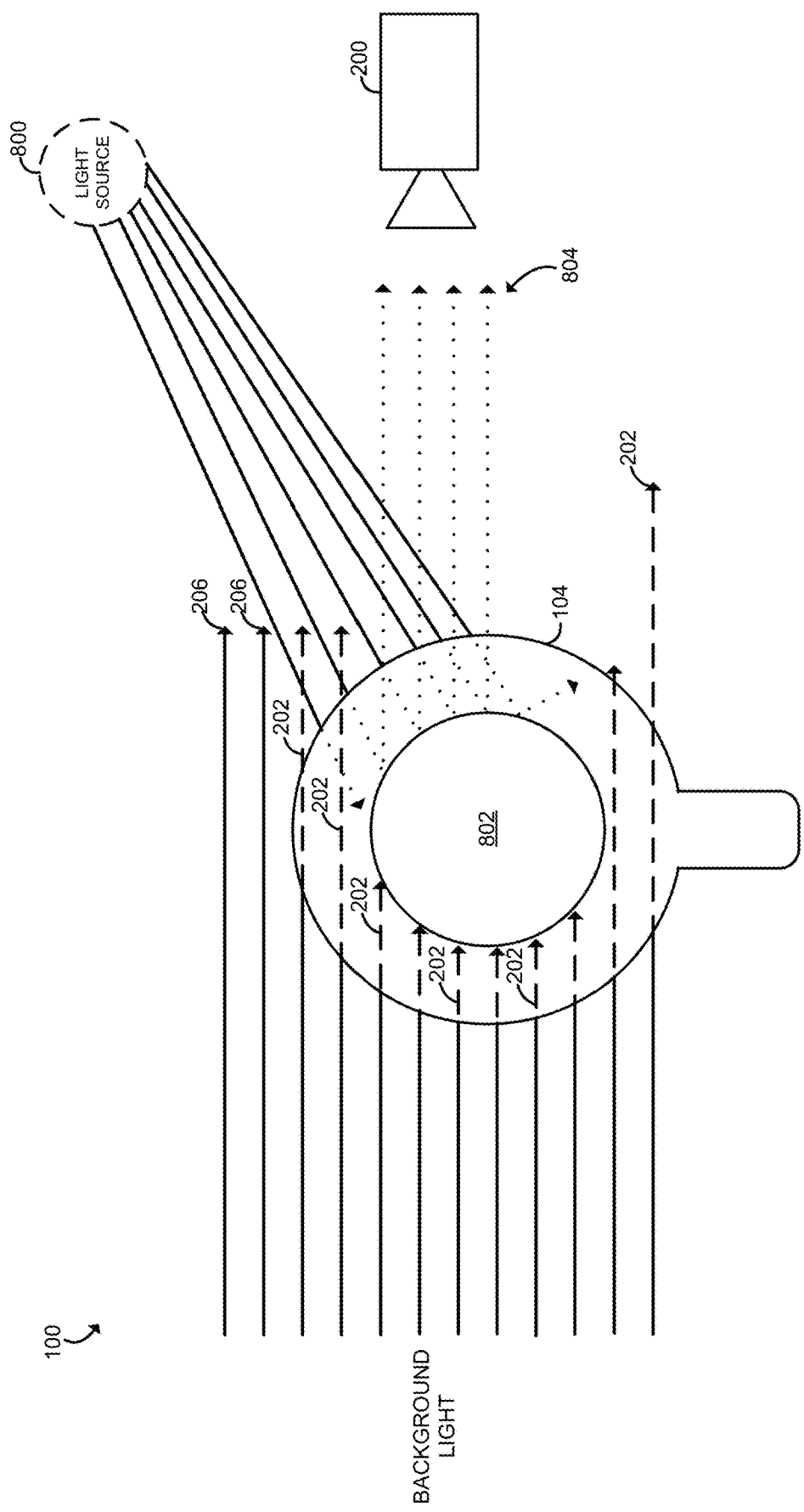
FIG. 8 is a is a cross-sectional, elevational view of at least one additional embodiment of an illumination marker including a diffusive core.

Referring now to FIG. 8, in some embodiments, the illumination marker 100 may be illuminated via passive lighting, rather than internal lighting. For example, in the illustrative embodiment of FIG. 8, the illumination marker 100 is configured to reflect light from an ambient light source 800. To do so, the illumination marker 100 of FIG. 8 includes a diffusive core 802, rather than the internal light source 102, which is surrounded by the optical attenuation cover 104. As described above, the optical attenuation cover 104 is configured to attenuate light passing through the cover 104. As such, the optical attenuation cover 104 attenuates both the background light traversing through the optical attenuation cover 104 (illustrated in FIG. 8 as dashed light rays 202), as well as the light from the light source 800 (illustrated in FIG. 8 as dotted light rays 804), a portion of which is reflected by the diffusive core 802 toward the camera 200. However, because the light from the light source 800 has a longer optical path through the optical attenuation cover 104 (i.e., the light traverses the cover 104 twice) compared to the light generated by an internal light source 102 (e.g., see FIG. 2), the optical attenuation cover 104 may be configured to attenuate light except for a defined wavelength band (i.e., a wavelength pass-band). In such embodiments, the ambient light source 800 may be configured to generate light within the wavelength pass-band of the optical attenuation cover 104 such that the attenuation of the light from the ambient light source 800 (dotted light rays 804) is significantly less than the attenuation of the background light (dashed light rays 202). As such, the light intensity of the light from the ambient light source 800 reflected back toward the camera 200 (dotted light rays 804) will be greater than the light intensity of the background light that has traversed through the optical attenuation cover 104 (dashed light rays 202).

Due to the differences in light intensity between the background light rays 202 and the reflected ambient light rays 804, the camera 200 may generate images having a higher contrast between the illumination marker 100 and the background light that has not traveled through the illumination marker 100 (i.e., background light rays 206 in FIG. 8). That is, the reduction of the intensity of the background light that has traversed through the illumination marker 100 (i.e., light rays 202) facilitates the discernibility of the diffusive core 802 of the illumination marker 100 in images generated by the camera 200. For example, the optical attenuation cover 104 of the illumination marker 100 may appear darker on a generated image relative to the background light (i.e., background light rays 206 in FIG. 8).

Figure 9:
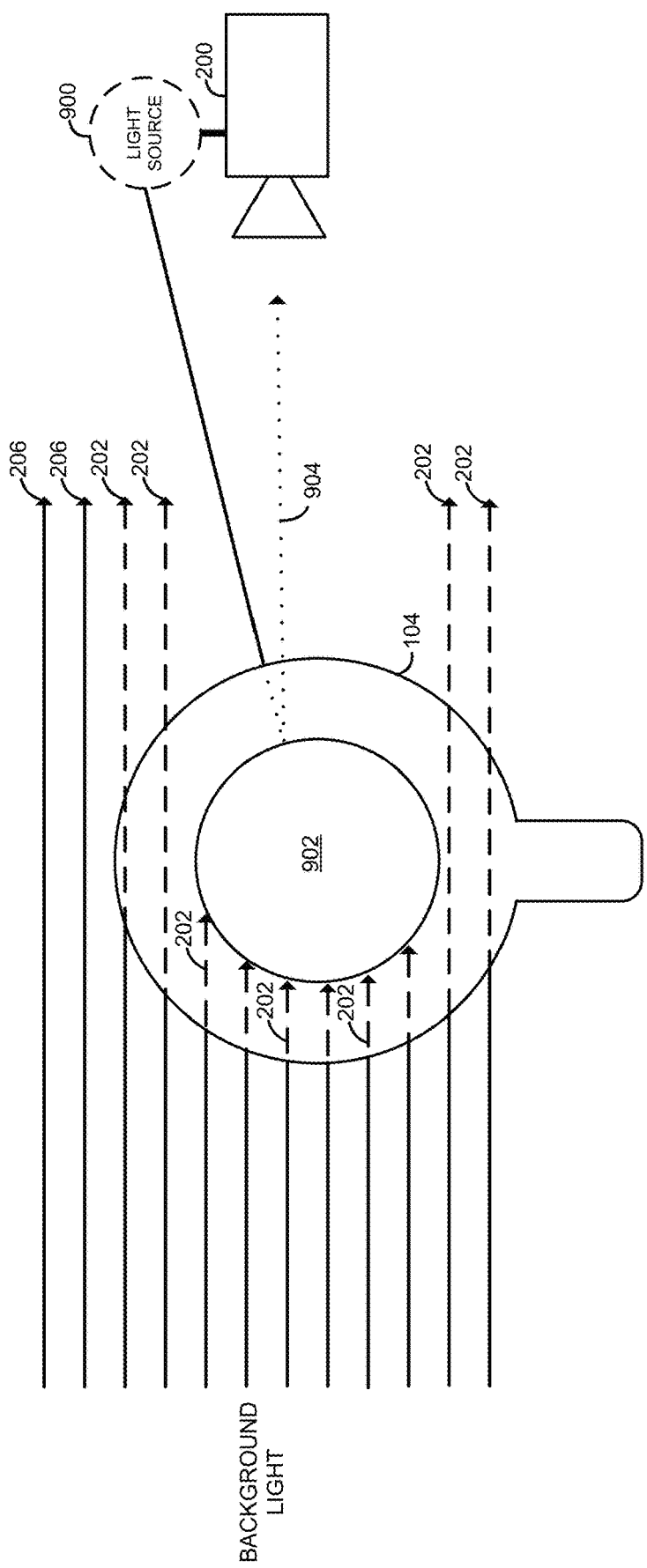
FIG. 9 is a cross-sectional, elevational view of at least one additional embodiment of an illumination marker including a retro-reflective core.

Referring now to FIG. 9, in other embodiments, the illumination marker 100 may be illuminated by an external light source 900 coupled to, or otherwise associated with, the camera 200. In such embodiments, the illumination marker 100 includes a retro-reflective core 902 configured to retro-reflect light received from the light source 900 back toward the camera 200. Again, as described above, the optical attenuation cover 104 is configured to attenuate light passing through the cover 104. As such, the optical attenuation cover 104 attenuates both the background light traversing through the optical attenuation cover 104 (illustrated in FIG. 9 as dashed light rays 202), as well as the light from the light source 900 (illustrated in FIG. 9 as dotted light rays 904). Because the light from the light source 900 has a longer optical path through the optical attenuation cover 104 (i.e., the light traverses the cover 104 twice) compared to the light generated by an internal light source 102 (e.g., see FIG. 2), the optical attenuation cover 104 may be configured to attenuate light except for a defined wavelength band (i.e., a wavelength pass-band) similar to the embodiment of FIG. 8. In such embodiments, the light source 900 may be configured to generate light within the wavelength pass-band of the optical attenuation cover 104 such that the attenuation of the light from the light source 900 (dotted light rays 904) is significantly less than the attenuation of the background light (dashed light rays 202) traversing through the optical attenuation cover 104. As such, the light intensity of the light from the light source 900 retro-reflected back toward the camera 200 (dotted light rays 904) will be greater than the light intensity of the background light that has traversed through the optical attenuation cover 104 (dashed light rays 202).

Again, due to the differences in light intensity between the background light rays 202 and the retro-reflected light rays 904, the camera 200 may generate images having a higher contrast between the illumination marker 100 and the background light that has not traveled through the illumination marker 100 (i.e., background light rays 206 in FIG. 9). That is, the reduction of the intensity of the background light that has traversed through the illumination marker 100 (i.e., light rays 202) facilitates the discernibility of the retro-reflective core 902 of the illumination marker 100 in images generated by the camera 200.

EXAMPLES

Illustrative examples of the technologies disclosed herein are provided below. An embodiment of the technologies may include any one or more, and any combination of, the examples described below.

Example 1 includes an illumination marker comprising a light source to generate light; and an optical attenuation cover coupled to the light source, wherein the optical attenuation cover is to attenuate an intensity of light that passes through the optical attenuation cover based on a length of an optical path of the light through the optical attenuation cover.

Example 2 includes the subject matter of Example 1, and wherein the optical attenuation cover is to attenuate an intensity of background light that passes through the optical attenuation cover at a greater amount than the optical attenuation cover attenuates an intensity of the light generated by the light source.

Example 3 includes the subject matter of Examples 1 or 2, and wherein the optical attenuation cover is formed from a polycarbonate material.

Example 4 includes the subject matter of any of Examples 1-3, and wherein the amount of attenuation of the intensity of light that passes through the optical attenuation is based on the wavelength of the light.

Example 5 includes the subject matter of any of Examples 1-4, and wherein the optical attenuation cover is to attenuate an intensity of light having a wavelength within a defined wavelength pass-band at an amount less than light having a wavelength outside of the defined wavelength pass-band.

Example 6 includes the subject matter of any of Examples 1-5, and, wherein the light source is to generate light having a wavelength within the defined wavelength pass-band.

Example 7 includes the subject matter of any of Examples 1-6, and wherein the light source is to generate light having a wavelength only within the defined wavelength pass-band.

Example 8 includes the subject matter of any of Examples 1-7, and wherein the light source is to generate light having a wavelength equal to 850 nanometers.

Example 9 includes the subject matter of any of Examples 1-8, and wherein the optical attenuation cover has a spherical shape.

Example 10 includes the subject matter of any of Examples 1-9, and wherein the optical attenuation cover is translucent.

Example 11 includes the subject matter of any of Examples 1-10, and wherein the light source is an incandescent light.

Example 12 includes the subject matter of any of Examples 1-11, and wherein the light source is an light emitting diode.

Example 13 includes the subject matter of any of Examples 1-12, and wherein the light source is omni-directional.

Example 14 includes the subject matter of any of Examples 1-13, and wherein the light source comprises a shell housed within the optical attenuation cover.

Example 15 includes the subject matter of any of Examples 1-14, and wherein the optical attenuation cover is secured to the shell.

Example 16 includes the subject matter of any of Examples 1-15, and wherein the optical attenuation cover has a thickness substantially equal to a radius of the shell.

Example 17 includes the subject matter of any of Examples 1-16, and wherein the shell has a spherical shape.

Example 18 includes the subject matter of any of Examples 1-17, and further comprising a base shaped to mate with a socket to provide electrical power to the light source.

Example 19 includes the subject matter of any of Examples 1-18, and wherein the optical attenuation cover comprises a physical barrier cover.

Example 20 includes the subject matter of any of Examples 1-19, and wherein the physical barrier cover comprises a plurality of light-blocking structures to block an amount of background light.

Example 21 includes the subject matter of any of Examples 1-20, and wherein plurality of light-blocking structures allow an amount of light generated by the light source to pass through the physical barrier cover.

Example 22 includes the subject matter of any of Examples 1-21, and wherein the plurality of light-blocking structures comprises plurality of polygonal structures having apertures through which the light generated by the light source can pass.

Example 23 includes an illumination marker comprising a diffusive core; and an optical attenuation cover coupled to the diffusive core, wherein the optical attenuation cover is to attenuate an intensity of light that passes through the optical attenuation cover based on a length of an optical path of the light through the optical attenuation cover, wherein the diffusive core is to reflect an amount of ambient light received by the diffusive core through the optical attenuation cover.

Example 24 includes the subject matter of Example 23, and wherein the diffusive core is formed from a diffusive material.

Example 25 includes the subject matter of Examples 23 or 24, and wherein the diffusive core has a spherical shape.

Example 26 includes the subject matter of any of Examples 23-25, and wherein the optical attenuation cover is to attenuate an intensity of background light that passes through the optical attenuation cover at a greater amount than the optical attenuation cover attenuates the ambient light reflected by the diffusive core.

Example 27 includes the subject matter of any of Examples 23-26, and wherein the optical attenuation cover is formed from a polycarbonate material.

Example 28 includes the subject matter of any of Examples 23-27, and wherein the amount of attenuation of the intensity of light that passes through the optical attenuation is based on the wavelength of the light.

Example 29 includes the subject matter of any of Examples 23-28, and wherein the optical attenuation cover is to attenuate an intensity of light having a wavelength within a defined wavelength pass-band at an amount less than light having a wavelength outside of the defined wavelength pass-band.

Example 30 includes the subject matter of any of Examples 23-29, and wherein the ambient light has a wavelength within the defined wavelength pass-band.

Example 31 includes an illumination marker comprising a retro-reflective core; and an optical attenuation cover coupled to the diffusive core, wherein the optical attenuation cover is to attenuate an intensity of light that passes through the optical attenuation cover based on a length of an optical path of the light through the optical attenuation cover, wherein the reflective core is to retro-reflect an amount of light generated by an external light source and received by the retro-reflective core through the optical attenuation cover.

Example 32 includes the subject matter of Example 31, and wherein the retro-reflective core is formed from a retro-reflective material.

Example 33 includes the subject matter of Examples 31 or 32, and wherein the retro-reflective core has a spherical shape.

Example 34 includes the subject matter of any of Examples 31-33, and wherein the optical attenuation cover is to attenuate an intensity of background light that passes through the optical attenuation cover at a greater amount than the optical attenuation cover attenuates the light generated by the external light source and retro-reflected by the retro-reflective core.

Example 35 includes the subject matter of any of Examples 31-34, and wherein the optical attenuation cover is formed from a polycarbonate material.

Example 36 includes the subject matter of any of Examples 31-35, and wherein the amount of attenuation of the intensity of light that passes through the optical attenuation is based on the wavelength of the light.

Example 37 includes the subject matter of any of Examples 31-36, and wherein the optical attenuation cover is to attenuate an intensity of light having a wavelength within a defined wavelength pass-band at an amount less than light having a wavelength outside of the defined wavelength pass-band.

Example 38 includes the subject matter of any of Examples 31-373, and wherein the light generated by the external light source has a wavelength within the defined wavelength pass-band.

Example 39 includes an object tracking system comprising an illumination marker coupled to an object to be tracked, wherein the illumination marker comprises (i) a light source to generate light and (ii) an optical attenuation cover coupled to the light source, wherein the optical attenuation cover is to attenuate an intensity of light that passes through the optical attenuation cover based on a length of an optical path of the light through the optical attenuation cover; and a camera to generate images of the illumination marker to track the object.

Example 40 includes the subject matter of Example 39, and wherein the optical attenuation cover is to attenuate an intensity of background light that passes through the optical attenuation cover at a greater amount than the optical attenuation cover attenuates the light generated by the light source.

Example 41 includes the subject matter of Examples 39 or 40, and wherein the optical attenuation cover is formed from a polycarbonate material.

Example 42 includes the subject matter of any of Examples 39-41, and wherein the amount of attenuation of the intensity of light that passes through the optical attenuation is based on the wavelength of the light.

Example 43 includes the subject matter of any of Examples 39-42, and wherein the optical attenuation cover is to attenuate an intensity of light having a wavelength within a defined wavelength pass-band at an amount less than light having a wavelength outside of the defined wavelength pass-band.

Example 44 includes the subject matter of any of Examples 39-43, and wherein the light generated by the light source has a wavelength within the defined wavelength pass-band.

Example 45 includes the subject matter of any of Examples 39-44, and wherein the light source is to generate light having a wavelength only within the defined wavelength pass-band.

Example 46 includes the subject matter of any of Examples 39-45, and wherein the light source is to generate light having a wavelength equal to 850 nanometers.

Example 47 includes the subject matter of any of Examples 39-46, and wherein the optical attenuation cover has a spherical shape.

Example 48 includes the subject matter of any of Examples 39-47, and wherein the optical attenuation cover is translucent.

Example 49 includes the subject matter of any of Examples 39-48, and wherein the light source is an incandescent light.

Example 50 includes the subject matter of any of Examples 39-49, and wherein the light source is an light emitting diode.

Example 51 includes the subject matter of any of Examples 39-50, and wherein the light source is omni-directional.

Example 52 includes the subject matter of any of Examples 39-51, and wherein the light source comprises a shell housed within the optical attenuation cover.

Example 53 includes the subject matter of any of Examples 39-52, and wherein the optical attenuation cover is secured to the shell.

Example 54 includes the subject matter of any of Examples 39-53, and wherein the optical attenuation cover has a thickness substantially equal to a radius of the shell.

Example 55 includes the subject matter of any of Examples 39-54, and wherein the shell has a spherical shape.

Example 56 includes the subject matter of any of Examples 39-55, and further comprising a base shaped to mate with a socket of the object to be tracked to provide electrical power to the light source.

Example 57 includes the subject matter of any of Examples 39-56, and wherein the optical attenuation cover comprises a physical barrier cover.

Example 58 includes the subject matter of any of Examples 39-57, and wherein the physical barrier cover comprises a plurality of light-blocking structures to block an amount of background light.

Example 59 includes the subject matter of any of Examples 39-58, and wherein plurality of light-blocking structures allow an amount of light generated by the light source to pass through the physical barrier cover.

Example 60 includes the subject matter of any of Examples 39-59, and wherein the plurality of light-blocking structures comprises plurality of polygonal structures having apertures through which the light generated by the light source can pass.

The invention claimed is:

1. An illumination marker comprising:
   a light source to generate light; and
   an optical attenuation cover coupled to the light source, wherein the optical attenuation cover is to attenuate an intensity of light that passes through the optical attenuation cover based on a length of an optical path of the light through the optical attenuation cover and wherein the optical attenuation cover is to attenuate an intensity of background light that passes through the optical attenuation cover at a greater amount than the optical attenuation cover attenuates an intensity of the light generated by the light source.

2. The illumination marker of claim 1, wherein the optical attenuation cover is formed from a polycarbonate material.

3. The illumination marker of claim 1, wherein the amount of attenuation of the intensity of light that passes through the optical attenuation is based on the wavelength of the light.

4. The illumination marker of claim 1, wherein the optical attenuation cover is to attenuate an intensity of light having a wavelength within a defined wavelength pass-band at an amount less than light having a wavelength outside of the defined wavelength pass-band.

5. The illumination marker of claim 1, wherein the light source is to generate light having a wavelength within the defined wavelength pass-band.

6. The illumination marker of claim 5, wherein the light source is to generate light having a wavelength only within the defined wavelength pass-band.

7. The illumination marker of claim 1, wherein the light source is omni-directional.

8. The illumination marker of claim 1, wherein the light source comprises a shell housed within the optical attenuation cover.

9. The illumination marker of claim 8, wherein the optical attenuation cover has a thickness substantially equal to a radius of the shell.

10. The illumination marker of claim 8, wherein each of the optical attenuation cover and the shell has a spherical shape.

11. The illumination marker of claim 1, wherein the optical attenuation cover comprises a physical barrier cover that includes a plurality of light-blocking structures to block an amount of background light, wherein the plurality of light-blocking structures comprises plurality of polygonal structures having apertures through which the light generated by the light source can pass without being blocked.

12. An illumination marker comprising:
    a diffusive core; and
    an optical attenuation cover coupled to the diffusive core, wherein the optical attenuation cover is to attenuate an intensity of light that passes through the optical attenuation cover based on a length of an optical path of the light through the optical attenuation cover,
    wherein the diffusive core is to reflect an amount of ambient light received by the diffusive core through the optical attenuation cover.

13. The illumination marker of claim 12, wherein the optical attenuation cover is to attenuate an intensity of background light that passes through the optical attenuation cover at a greater amount than the optical attenuation cover attenuates the ambient light reflected by the diffusive core.

14. The illumination marker of claim 12, wherein the optical attenuation cover is formed from a polycarbonate material.

15. The illumination marker of claim 12, wherein the amount of attenuation of the intensity of light that passes through the optical attenuation is based on the wavelength of the light.

16. The illumination marker of claim 12, wherein the optical attenuation cover is to attenuate an intensity of light having a wavelength within a defined wavelength pass-band at an amount less than light having a wavelength outside of the defined wavelength pass-band.

17. An illumination marker comprising:
    a retro-reflective core; and
    an optical attenuation cover coupled to the diffusive core, wherein the optical attenuation cover is to attenuate an intensity of light that passes through the optical attenuation cover based on a length of an optical path of the light through the optical attenuation cover,
    wherein the reflective core is to retro-reflect an amount of light generated by an external light source and received by the retro-reflective core through the optical attenuation cover.

18. The illumination marker of claim 17, wherein the optical attenuation cover is to attenuate an intensity of background light that passes through the optical attenuation cover at a greater amount than the optical attenuation cover attenuates the light generated by the external light source and retro-reflected by the retro-reflective core.

19. The illumination marker of claim 17, wherein the optical attenuation cover is formed from a polycarbonate material.

20. The illumination marker of claim 17, wherein the amount of attenuation of the intensity of light that passes through the optical attenuation is based on the wavelength of the light.

21. The illumination marker of claim 17, wherein the optical attenuation cover is to attenuate an intensity of light having a wavelength within a defined wavelength pass-band at an amount less than light having a wavelength outside of the defined wavelength pass-band.

22. An object tracking system comprising:
an illumination marker coupled to an object to be tracked, wherein the illumination marker comprises (i) a light source to generate light and (ii) an optical attenuation cover coupled to the light source, wherein the optical attenuation cover is to attenuate an intensity of light that passes through the optical attenuation cover based on a length of an optical path of the light through the optical attenuation cover and wherein the optical attenuation cover is to attenuate an intensity of background light that passes through the optical attenuation cover at a greater amount than the optical attenuation cover attenuates an intensity of the light generated by the light source; and
a camera to generate images of the illumination marker to track the object.

23. The object tracking system of claim 22, wherein the amount of attenuation of the intensity of light that passes through the optical attenuation is based on the wavelength of the light.

* * * * *